United States Patent

Riefling et al.

[11] Patent Number: 4,885,372
[45] Date of Patent: Dec. 5, 1989

[54] CYCLOPENTANE DERIVATIVES, METHODS FOR PRODUCING THEM AND THEIR USE

[75] Inventors: Bernhard Riefling, Darmstadt; Hans Witzel, Dieburg, both of Fed. Rep. of Germany

[73] Assignee: Merck Patent Gesellschaft mit Beschränkter Haftung, Darmstadt, Fed. Rep. of Germany

[21] Appl. No.: 909,745

[22] Filed: Sep. 19, 1986

[30] Foreign Application Priority Data

Sep. 20, 1985 [DE] Fed. Rep. of Germany ....... 3533576

[51] Int. Cl.⁴ ...................... C07F 7/08; C07D 303/02
[52] U.S. Cl. ..................................... 549/215; 556/449
[58] Field of Search .................. 556/449; 549/215; 568/838

[56] References Cited

U.S. PATENT DOCUMENTS 4,069,387 1/1978 Hayashi et al. ................. 556/449 X
4,085,272 4/1978 Weiss et al. ...................... 556/449 X
4,113,967 9/1978 Weiss ............................... 556/449 X Primary Examiner—Paul F. Shaver
Attorney, Agent, or Firm—Millen, White & Zelano

[57] ABSTRACT

New cyclopentane derivatives of the formula I

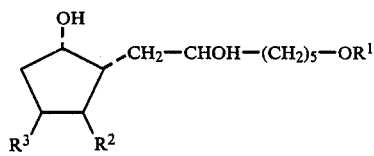

in which
R$^1$ is H or a hydroxyl protective group, and
R$^2$ and R$^3$ are together an O atom or are together a bond, can be used in the preparation of prostaglandin derivatives.

9 Claims, No Drawings

CYCLOPENTANE DERIVATIVES, METHODS FOR PRODUCING THEM AND THEIR USE

This invention relates to novel cyclopentane derivatives, a process for their production and their use in the preparation of prostaglandin compounds.

SUMMARY OF THE INVENTION

It is an object of the invention to provide a new process and new intermediates for the preparation of the acid "A" defined below and related compounds and thus for the preparation of prostaglandin derivatives, which process does not have the disadvantages of known processes, or has them only to a lesser extent, and which provides high yields and is suitable for industrial scale.

Upon further study of the specification and appended claims, further objects and advantages of this invention will become apparent to those skilled in the art.

These and other objects have been attained by providing new cyclopentane derivatives of the formula I

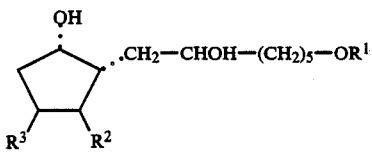

in which
R$^1$ is H or a hydroxyl protective group, and
R$^2$ and R$^3$ are together an O atom or are together a bond,
and a process for their preparation, characterized in that a lactol of the formula II

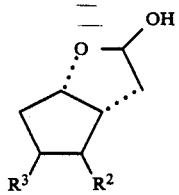

in which
R$^2$ and R$^3$ have the above-mentioned meanings, is reacted with a compound of the formula III

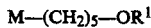

M—(CH$_2$)$_5$—OR$^1$     (III)

in which
M is MgHal or Li and
Hal is Cl, Br or I, and
R$^1$ has the above-mentioned meaning,
and where appropriate, a resulting compound of the formula I where R$^2$+R$^3$=a bond is converted by treatment with an oxidizing agent into a compound of the formula I where R$^2$+R$^3$=O).

The compounds of the formula I can be used as intermediates in the preparation of prostaglandin derivatives. In particular, it is possible to obtain from I (R$^2$+R$^3$=O) 6-oxo-7-(2α,3α-epoxy-5-oxo-1α-cyclopentyl)heptanoic acid ("A") from which, for example, 6,9-diketo-13-thiaprostaglandins can be prepared (German Offenlegungsschrift No. 3,401,542, which disclosure is incorporated by reference herein).

Additionally, as described more fully below, compounds of formula I wherein R$^2$ and R$^3$ together are an additional bond can be used to make compounds wherein R$^2$ and R$^3$ together are O. Compounds of formula I wherein R$^1$ is a hydroxyl protective group can be employed to make compounds wherein R$^1$ is H.

A three-step synthesis is given in loc.cit. for the preparation of the acid "A", the synthesis starting from 2α-(6-carboxy-cis-2-hexenyl)-3α,4α-epoxy-1α-cyclopentanol. However, the yields in this synthesis are unsatisfactory, especially in attempting to transfer it to the industrial scale.

DETAILED DESCRIPTION

It has been found that the new process, which starts with readily accessible compounds (II), provides better yields than the known process and can be transferred without difficulty to the industrial scale.

The radical R$^1$ in the compounds of the formulae I and III can be a hydroxyl protective group. The term "hydroxyl protective group" is generally known and designates a group which is suitable for protection (blocking) of the hydroxyl group from chemical reactions but which can readily be removed after the desired chemical reaction elsewhere in the molecule has been carried out. The nature and size of the hydroxyl protective groups are not critical since they are removed again after the desired chemical reaction or sequence of reactions.

Examples of suitable hydroxyl protective groups are unsubstituted or substituted acyl groups, ether groups or silyl ether groups. Preferred hydroxyl protective groups are trialkylsilyl having a total of 3-12 C atoms, preferably trimethylsilyl, triethylsilyl, triisopropylsilyl, tert.-butyldimethylsilyl, di-tert.-butylmethylsilyl; aryldialkylsilyl having a total of 8-18 C atoms, preferably phenyldimethylsilyl; tetrahydro-2-pyranyl; alkoxymethyl having 2-5 C atoms, such as methoxymethyl, ethoxymethyl or tert.-butoxymethyl; alkylthiomethyl having 2-5 C atoms, such as methylthiomethyl, ethylthiomethyl or tert.-butylthiomethyl; aryloxymethyl having 7-11 C atoms, such as phenoxymethyl; also alkyl having 1-7 C atoms, preferably tert.-butyl, methyl, ethyl or propyl, as well as isopropyl, butyl, isobutyl, sec.-butyl, pentyl, hexyl or heptyl; acyl having 1-10 C atoms, in particular alkanoyl having 1-6 C atoms, such as formyl, acetyl, trimethylacetyl, tert.-butylacetyl; aroyl having 7-10 C atoms, such as benzoyl; furthermore carbonic ester groups such as tert.-butoxycarbonyl or benzoxycarbonyl. R$^1$ is particularly preferably a trimethylsilyl group. The hydroxyl protective group can be inserted and removed conventionally. It can also be removed directly during the oxidation stage discussed below, e.g. with "Jones reagent".

The lactols of the formula II, which can be obtained by reduction of the corresponding lactones with diisobutylaluminum hydride, include the preferred 2-oxa-1βH,5βH-bicyclo[3.3.0]oct-5-en-3-ol (IIa) and the two stereoisomeric 2-oxa-6,7-epoxybicyclo[3.3.0]octan-3-ols.

The reaction is fully conventional and is performed according to known methods, method cf. L. F. Fieser and M. Fieser, Reagents for Organic Synthesis, John Wiley and Sons, Inc., New York, 1967, p. 261. The organometallic compounds of the formula III can be obtained from 5-Hal-pentanols, which can first be converted by protection of the OH group into compounds of the formula Hal—(CH$_2$)$_5$—OR$^1$; the latter can then be reacted with Li or Mg. These reactions are fully conventional also.

The reaction of the compounds of the formulae II and III is preferably carried out in the presence of an inert solvent, for example an ether such as tetrahydrofuran (THF), diethyl ether, diisopropyl ether or methyl tert.-butyl ether, at temperatures between about 0° and 100°, preferably between 15° and 30°. It is preferable for the organometallic compound III to be prepared in situ; the lactol II or a solution thereof is then added.

A cyclopentene derivative I ($R^2+R^3$=bond) thus obtained can, if desired, be oxidized to the corresponding epoxide I ($R^2+R^3$=O). Particularly suitable oxidizing agents are peroxides and hydroperoxides such as m-chloroperbenzoic acid or tert.-butyl hydroperoxide. Hydroperoxides are preferably used in the presence of a catalyst, for example a heavy metal catalyst such as molybdenum hexacarbonyl, vanadium(IV) oxide or one of its derivatives, for example vanadium-(IV) oxide acetylacetonate. The epoxidation is preferably carried out in the presence of an inert solvent, for example a halogenated hydrocarbon such as dichloromethane, chloroform, carbon tetrachloride or trichloroethylene, or an aromatic hydrocarbon such as benzene or toluene, at temperatures between about 0° and about 40°, preferably between 15° and 30° C.

It is also possible to carry out the epoxidation in several steps, for example by addition of HOBr to give the bromohydrin followed by dehydrobromination to give the epoxide.

The diols of the formula I which can be obtained according to the invention can be oxidized to corresponding diketo compounds. Oxidation of I ($R^1$=trimethylsilyl, $R^2+R^3$=O) with "Jones reagent" (CrO$_3$ in aqueous sulphuric acid), for example, results in the known acid "A" (loc.cit.).

In the examples, "usual working-up" means: extraction with ethyl acetate or dichloromethane, washing with water, drying of the organic phase and evaporation thereof.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the preceding text and the following examples, all temperatures are set forth uncorrected in degrees Celsius and all parts and percentages are by weight; unless otherwise indicated.

EXAMPLE 1

(a) A solution of 1795 g of 5-trimethylsilyloxypentyl bromide (obtainable from 5-bromopentanol and chlorotrimethylsilane) in 1.6 l of THF is added dropwise within two hours to a boiling mixture of 243 g of Mg turnings, 200 mg of iodine and 1 l of THF under nitrogen, and the mixture is then allowed to cool. Then, at 20°-22°, a solution of 315 g of IIa in 1 l of THF is added dropwise within two hours. The mixture is then stirred for one hour, poured into saturated NH$_4$Cl solution, the usual working-up is carried out (ethyl acetate), and 811 g of crude 2α-(2-hydroxy-7-trimethylsilyloxyheptyl)-3-cyclopenten-1-ol (B) are obtained.

(b) 200 g of CaCO$_3$ and 3 g of vanadium(IV) oxide acetylacetonate ("VA") are added to a solution of 650 g of (b) in 3.25 l of dichloromethane. 628 ml of 70% aqueous tert.-butyl hydroperoxide are added dropwise at 20°, with stirring, within 45 min.; simultaneously, further VA is added in portions, totalling 45 g. The mixture is then stirred for 5 hours, poured into saturated Na$_2$S$_2$O$_3$ solution, and filtration and the usual working-up are carried out (dichloromethane), and 685 g of crude 2α-(2-hydroxy-7-trimethylsilyloxyheptyl)-3α,4α-epoxy-1α-cyclopentanol are obtained.

EXAMPLE 2

2.7 l of Jones reagent (obtained by stirring 721 g of CrO$_3$ into 621 ml of concentrated H$_2$SO$_4$ and making up with water) are added dropwise within 3.5 hours to a solution, at $-2°$, of 665 g of the above-mentioned compound in a mixture of 5.32 l of acetone and 5.32 l of THF. The mixture is then stirred at 0° for one hour, 800 ml of isopropanol are added while cooling, and the mixture is stirred for a further 30 min, 1 l of water is added, and separation and extraction with dichloromethane are carried out. The combined organic phases are washed with saturated NaCl solution, dried and evaporated. The residue is purified by chromatography. 6-oxo-7-(2α,3α-epoxy-5-oxo-1α-cyclopentyl)heptanoic acid ("A"), m.p. 93°-94°, is obtained.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A cyclopentane derivative of the formula

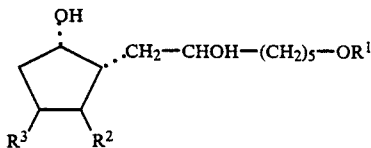

wherein
$R^1$ is H or a hydroxyl protective group, and
$R^2$ and $R^3$ together form an epoxy group or together form a double bond.

2. A cyclopentane derivative of claim 1, wherein $R^1$ is H and $R^2$ and $R^3$ together form a double bond.

3. A cyclopentane derivative of claim 1, wherein $R^1$ is a hydroxyl protective group and $R^2$ and $R^3$ together form a double bond.

4. A cyclopentane derivative of claim 1, wherein $R^1$ is H and $R^2$ and $R^3$ together are an epoxy group.

5. A cyclopentane derivative of claim 1, wherein $R^1$ is a hydroxyl protective group and $R^2$ and $R^3$ together are an epoxy group.

6. A compound of claim 3, wherein $R^1$ is trimethylsilyl.

7. A compound of claim 5, wherein $R^1$ is trimethylsilyl.

8. 2α-(2-Hydroxy-7-trimethylsilyloxyheptyl)-3-cyclopenten-1α-ol, a compound of claim 1.

9. 2α-(2-Hydroxy-7-trimethylsilyloxyheptyl)-3α-4α-epoxy-1α-cyclopentanol, a compound of claim 1.

* * * * *